United States Patent [19]
Tsuchida et al.

[11] Patent Number: 5,515,723
[45] Date of Patent: May 14, 1996

[54] HUMIDITY METER

[75] Inventors: Atsuko Tsuchida; Shiro Nakagawa, both of Tokyo, Japan

[73] Assignee: TDK Corporation, Tokyo, Japan

[21] Appl. No.: 383,314

[22] Filed: Feb. 3, 1995

[30] Foreign Application Priority Data

Feb. 17, 1994 [JP] Japan .................................. 6-020628

[51] Int. Cl.$^6$ ................................................ G01N 19/100
[52] U.S. Cl. ................................. 73/335.020; 73/29.020
[58] Field of Search .............................. 73/29.02, 335.02; 338/35

[56] References Cited

U.S. PATENT DOCUMENTS

| | | | |
|---|---|---|---|
| 4,330,718 | 5/1982 | Kinomoto et al. | 307/118 |
| 4,386,336 | 5/1983 | Kinomoto et al. | 338/35 |
| 4,801,211 | 1/1989 | Yagi et al. | 374/28 |
| 5,065,625 | 11/1991 | Nakagawa et al. | |
| 5,317,274 | 5/1994 | Nakagawa et al. | |
| 5,396,796 | 3/1995 | Kotani et al. | 73/335.02 |

*Primary Examiner*—Hezron E. Williams
*Assistant Examiner*—Jay L. Politzer
*Attorney, Agent, or Firm*—Oblon, Spivak, McClelland, Maier & Neustadt

[57] ABSTRACT

A humidity sensor 1 has an impedance Zs thereof changed exponentially with respect to a relative humidity. A z–f conversion circuit 2 generates a pulse signal S1 corresponding to the impedance Zs. A time constant controlled differentiating circuit 3 has an impedance Zt of a voltage control variable impedance element 32 changed exponentially by a control voltage Vc, and outputs a differentiated signal S2 obtained by differentiating the pulse signal S1. A waveform shaping circuit 4 outputs a pulse signal train S3 obtained by binary-coding the differentiated signal S2. An integrating circuit 5 causes a first integrating circuit 51 to obtain the control voltage Vc by integrating the pulse signal train S3 and causes a second integrating circuit 52 to obtain a humidity signal S4 by integrating the pulse signal train S3. A bias circuit 6 applies a bias voltage to a control terminal 323 of the voltage control variable impedance element 32.

11 Claims, 10 Drawing Sheets

HUMIDITY METER

BACKGROUND OF THE INVENTION

The invention relates to a humidity meter or a hygrometer which provides a DC potential proportional to the measured humidity, and in particular, relates to a meter which improves a linear relationship between humidity and an output DC potential.

Conventionally, a humidity meter adapted for use in various kinds of electronic apparatuses such as copying machines and printers is known. The humidity meter uses an impedance variable humidity sensor whose impedance varies with changing humidity. Since the impedance variable humidity sensor has a characteristic that the impedance thereof varies exponentially with respect to the relative humidity, nonlinearity of the humidity sensor must be corrected in order to linearize the humidity-output voltage characteristic when put in actual use. It is common to use a logarithmic amplifier as a linearizing means. More recently known, is an inexpensive linearizing technique using no logarithmic amplifier such as disclosed in U.S. Pat. Nos. 5,065,625 and 5,317,274. In these conventional art devices, the relationship between the base voltage and emitter current of a transistor serving as a voltage control variable impedance element is exponential and that the impedance thereof varies exponentially. That is, nonlinearity of the humidity sensor is corrected by the aforementioned characteristic of the transistor.

However, the aforementioned conventional humidity meters have the following problems.

Since the impedance of the transistor is controlled by the integrated output of an integrating circuit, the base-emitter voltage of the transistor is insufficient when the integrated output, i.e., in the low humidity range. As a result, impedance control of the transistor is not satisfactory, thereby resulting in insufficient linearization of the relative humidity-output voltage characteristic.

In a case where a diode is connected to the emitter of the transistor in series in order to compensate the unsatisfactory nonlinearity of the transistor, a forward voltage of the diode is applied which is unnegligible. Therefore, the insufficient linearization of humidity meters in the range of a small integrated output is unresolved.

SUMMARY OF THE INVENTION

Accordingly, an object of the invention is to provide a humidity meter capable of outputting a linearized humidity signal.

Another object of the invention is to provide a humidity meter capable of outputting a humidity signal having high linearity not only by ensuring reliable operation of the voltage control variable impedance element in the low output range, but also by preventing variations from adversely affecting the operation.

Still another object of the invention is to provide a humidity meter capable of outputting a humidity signal having high linearity in the low output range by correcting unsatisfactory linearity of the voltage control variable impedance element.

To achieve the above objects, the invention is applied to a humidity meter that includes: a humidity sensor; an impedance-frequency conversion circuit; a time constant controlled differentiating circuit; a waveform shaping circuit; an integrating circuit; and a bias circuit.

The humidity sensor has an impedance which is changed exponentially with respect to a relative humidity. The impedance-frequency conversion circuit generates a pulse signal whose frequency corresponds to the impedance of the humidity sensor. The time constant controlled differentiating circuit receives the output of the impedance-frequency conversion circuit and includes a capacitor and a voltage control variable impedance element, and has the capacitor and the voltage control variable impedance element connected in series with each other. The voltage control variable impedance element is implemented by a three-terminal element having main electrodes and a control electrode, and an impedance thereof is changed exponentially by a voltage applied to the control electrode. A differentiated signal obtained by differentiating the pulse signal is outputted from both terminals of the main electrodes.

The waveform shaping circuit receives the differentiated signal and outputs a pulse signal train, which is obtained by binary-coding the differentiated signal by a predetermined voltage. The integrating circuit includes a first integrating circuit and a second integrating circuit. The first integrating circuit integrates the inputted pulse signal train and supplies a voltage obtained by the integration to the control electrode of the voltage control variable impedance element as the control voltage, and the second integrating circuit integrates the pulse signal train and outputs a voltage obtained by the integration as a humidity signal.

The bias circuit applies a bias voltage to the control electrode.

It is preferred that the bias circuit be operated by the pulse signal train as a power supply thereof.

As another preferred embodiment, the time constant controlled differentiating circuit includes a nonlinear impedance element whose impedance is changed exponentially by an applied voltage; the nonlinear impedance element is connected to the main electrode opposite to the main electrode to which the capacitor is connected; and the differentiated signal is outputted from both terminals of the voltage control variable impedance element and the nonlinear impedance element which are connected in series with each other.

As still another preferred embodiment, the voltage control variable impedance element is implemented by a transistor; the nonlinear impedance element is implemented by a diode; the anode of the diode is connected to the emitter of the transistor; and the capacitor is connected to the collector of the transistor; and the control voltage and the bias voltage are applied to the base of the transistor.

As still another preferred embodiment, the time constant controlled differentiating circuit has an impedance adjusting circuit; and the impedance adjusting circuit is connected in parallel with the nonlinear impedance element.

As still another preferred embodiment, the impedance adjusting circuit includes a capacitor, a resistor, or a diode.

The humidity sensor has an impedance thereof changed exponentially with respect to a relative humidity, and the impedance-frequency conversion circuit generates a pulse signal whose frequency corresponds to the impedance of the humidity sensor. Therefore, a pulse signal whose frequency is changed exponentially with respect to a relative humidity can be obtained from the impedance-frequency conversion circuit.

The time constant controlled differentiating circuit has the capacitor and the voltage control variable impedance element connected in series with each other; the voltage control variable impedance element is implemented by a three-terminal element having main electrodes and a control electrode; the impedance of the voltage controlled variable impedance element is changed exponentially by a voltage applied to the control electrode; and a differentiated signal obtained by differentiating the pulse signal is outputted from both terminals of the main electrodes. Therefore, a differentiated signal, which follows changes in the impedance of the voltage control variable impedance element and whose time constant changes exponentially, can be obtained.

The waveform shaping circuit receives the differentiated signal, whose time constant changes exponentially, and outputs a pulse signal train obtained by binary-coding the differentiated signal by a predetermined voltage. Therefore, a pulse signal train having a pulse width, that is obtained by compressing the pulse width of the pulse signal logarithmically with respect to the frequency, can be obtained from the waveform shaping circuit.

In the integrating circuit, the first integrating circuit integrates the inputted pulse signal train and supplies a voltage obtained by the integration to the control electrode of the voltage control variable impedance element as the control voltage. Therefore, when the pulse width of the pulse signal train is increased to increase the control voltage, the impedance of the voltage control variable impedance is decreased. As a result, the pulse width of the pulse signal train obtained from the waveform shaping circuit is decreased, thereby checking the control voltage from increasing. Conversely, when the pulse width of the pulse signal train is decreased to decrease the control voltage, the impedance of the voltage control variable impedance is increased. As a result, the pulse width of the pulse signal train obtained from the waveform shaping circuit is increased, thereby checking the control voltage from decreasing. That is, the first integrating circuit degenerates the time constant controlled differentiating circuit, which in turn stabilizes the pulse signal train.

The second integrating circuit integrates the pulse signal train and outputs a voltage obtained by the integration as a humidity signal. Therefore, a linearized relative humidity-output voltage characteristic can be obtained.

Since the bias circuit applies a bias voltage to the control electrode, the voltage control variable impedance element can be operated appropriately even if the control voltage is low. Therefore, a shortage of the control voltage can be supplemented by the application of the bias voltage, which in turn allows the voltage control variable impedance element to be operated, allows (i.e., the impedance of the voltage control variable impedance element to change exponentially). As a result, a differentiated signal whose time constant changes exponentially can be obtained from both terminals of the main electrodes of the voltage control variable impedance element. This operation not only ensures reliable operation of the voltage control variable impedance element in the low output range, but also prevents variations from adversely affecting the operation, so that a relative humidity signal having high linearity can be obtained.

In the case where the bias circuit is operated by the pulse signal train as a power supply thereof, the bias voltage is applied to the control terminal only when the voltage control variable impedance element is operated to differentiate the pulse signal. Therefore, the bias voltage is applied only when the application of the bias voltage is necessary, which in turn allows the control characteristic of the voltage control variable impedance element to be improved. Since the peak value of the pulse signal train becomes larger than the control voltage integrated at the time the differentiation is started, the bias circuit can apply a bias voltage to the control terminal. In addition, power consumption of the bias circuit can be reduced as well.

In the case where the time constant controlled differentiating circuit includes a nonlinear impedance element whose impedance is changed exponentially by an applied voltage; the nonlinear impedance element is connected to the main electrode opposite to the main electrode to which the capacitor is connected; and a differentiated signal is outputted from both terminals of the voltage control variable impedance element and the nonlinear impedance element which are connected in series with each other. In that case, a shortage in the impedance of the conventional voltage control variable impedance element can be supplemented by the nonlinear impedance element in correcting the nonlinearity of the humidity sensor, which in turn allows a differentiated signal to be obtained. The differentiated signal follows changes in the impedances of the voltage control variable impedance element and the nonlinear impedance element and having a time constant thereof changed exponentially. Required at this instance is a control voltage that is equal to a value obtained by adding a voltage drop of the nonlinear impedance element to a voltage drop between the control electrode and the main electrode of the voltage control variable impedance element. It is the bias circuit 6 supplementing the control voltage that ensures reliable operation of the voltage control variable impedance element and the nonlinear impedance element. The application of the control voltage degenerates the voltage control variable impedance element and the nonlinear impedance element, which in turn improves linearity of the relative humidity signal. The application of the bias voltage by the bias circuit allows a relative humidity signal having high linearity to be obtained not only by ensuring reliable operation of the voltage control variable impedance element and the nonlinear impedance element in the low output range, but also by preventing variations from adversely affecting the operation.

In the embodiment in which the voltage control variable impedance element is implemented by a transistor; the nonlinear impedance element is implemented by a diode; the anode of the diode is connected to the emitter of the transistor; the capacitor is connected to the collector of the transistor; and the control voltage and the bias voltage are applied to the base of the transistor, the application of the control voltage degenerates the voltage control variable impedance element and the nonlinear impedance element, which in turn allows linearity of the relative humidity signal to be improved. As a result, a relative humidity signal having high linearity can be obtained not only by ensuring reliable operation of the voltage control variable impedance element and the nonlinear impedance element in the low output range, but also by preventing variations from adversely affecting the operation.

In the embodiment in which the time constant controlled differentiating circuit includes an impedance adjusting circuit; and the impedance adjusting circuit is connected in parallel with the nonlinear impedance element, the impedance of the nonlinear impedance element can be finely adjusted.

In the embodiment in which the impedance adjusting circuit is implemented by a capacitor, the impedance of the nonlinear impedance element can be finely adjusted in accordance with the frequency of the pulse signal.

In the embodiment in which the impedance adjusting circuit is implemented by a resistor, the impedance of the nonlinear impedance element can be finely adjusted irrespective of the frequency of the pulse signal.

In the embodiment in which the impedance adjusting circuit is implemented by a diode, the impedance of the nonlinear impedance element can be adjusted to a value that is equal to the reciprocal of an integer.

DETAILED DESCRIPTION OF THE PREFERRED EMBODIMENTS

Figure 1:
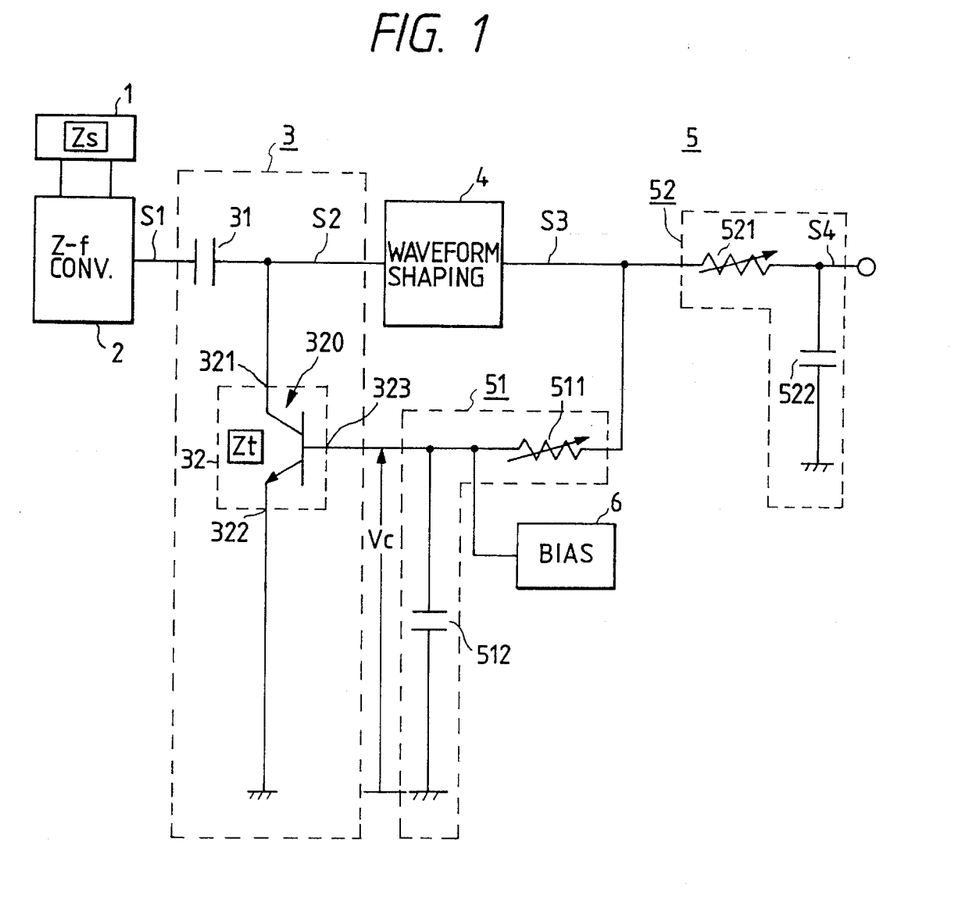
FIG. 1 is a block diagram of a humidity meter, which is an embodiment of the invention.

FIG. 1 is a block diagram of a humidity meter of the invention. In FIG. 1, reference numeral 1 denotes a humidity sensor; 2, an impedance-frequency conversion circuit (hereinafter referred to as "z–f conversion circuit"); 3, a time constant controlled differentiating circuit; 4, a waveform shaping circuit; 5, an integrating circuit; and 6, a bias circuit.

The humidity sensor 1 has an impedance Zs thereof changed exponentially with respect to a relative humidity. The humidity sensor 1 according to this embodiment is preferably made of a high-weight molecular material, and exhibits low impedance at high humidity and high impedance at low humidity. Specifically, the impedance of the humidity sensor 1 ranges from $10^4$ to $10^7$ [Ω].

The z–f conversion circuit 2 generates a pulse signal S1 whose frequency corresponds to the impedance Zs of the humidity sensor 1. When the impedance Zs is low, the frequency becomes high, whereas when the impedance Zs is high, the frequency becomes low.

The time constant controlled differentiating circuit 3 includes a capacitor 31 and a voltage control variable impedance element 32. The capacitor 31 is connected in series with the voltage control variable impedance element 32. The voltage control variable impedance element 32 consists of a three-terminal element having main electrodes 321, 322, and a control electrode 323, and has an impedance Zt thereof exponentially changed in accordance with a control voltage Vc applied to the control electrode 323. The time constant controlled differentiating circuit 3 outputs a differentiated signal S2, which is a signal obtained by differentiating the pulse signal S1, from both terminals of the main electrodes 321, 322 of the voltage control variable impedance element 32.

The waveform shaping circuit 4 receives the differentiated signal S2, and outputs a pulse signal train S3 obtained by binary-coding the differentiated signal S2, a binary "1" being represented by a predetermined voltage.

The integrating circuit 5 includes a first integrating circuit 51 and a second integrating circuit 52. The first integrating circuit 51 integrates the inputted pulse signal train S3, and supplies a voltage, obtained by the integration, to the control electrode 323 of the voltage control variable impedance element 32 as the control voltage Vc. Specifically, the first integrating circuit 51 has a resistor 511 and a capacitor 512, and the terminal voltage of the capacitor 512 is set to the control voltage Vc. The second integrating circuit 52 integrates the pulse signal train S3, and outputs a voltage obtained by the integration as a humidity signal S4. Specifically, the second integrating circuit 52 has a resistor 521 and a capacitor 522. The terminal voltage of the capacitor 522 serves as the humidity signal S4.

The bias circuit 6 applies a bias voltage to the control electrode 323 of the voltage control variable impedance element 32.

Since the humidity sensor 1 has the impedance Zs thereof changed exponentially with respect to the relative humidity and the z–f conversion circuit 2 generates the pulse signal S1 whose frequency corresponds to the impedance Zs of the humidity sensor 1 as described above, the pulse signal S1 whose frequency is changed exponentially with respect to the relative humidity can be obtained from the z–f conversion circuit 2.

The time constant controlled differentiating circuit 3 is designed so that the capacitor 31 is connected in series with the voltage control variable impedance element 32; the voltage control variable impedance element 32 consists of the three-terminal element having the main electrodes 321, 322 and the control electrode 323; the impedance Zt is changed exponentially by the control voltage Vc applied to the control electrode 323; and the differentiated signal S2 obtained by differentiating the pulse signal S1 is outputted from both terminals of the main electrodes 321, 322. Therefore, the differentiated signal S2 which follows changes in the impedance of the voltage control variable impedance element 32 and whose time constant changes exponentially can be obtained.

The waveform shaping circuit 4 is designed so that the differentiated signal S2 whose time constant changes exponentially is received; and the pulse signal train S3 obtained by binary-coding the differentiated signal S2 by a predetermined voltage is outputted. Therefore, the pulse signal train S3 having a pulse width obtained by compressing the pulse width of the pulse signal S1 logarithmically with respect to the frequency can be obtained from the waveform shaping circuit 4.

The integrating circuit 5 is designed so that the first integrating circuit 51 thereof integrates the inputted pulse signal train S3 and supplies the voltage obtained by the integration to the control electrode 323 of the voltage control variable impedance element 32 as the control voltage Vc. Therefore, when the pulse width of the pulse signal train S3 is increased to increase the control voltage Vc, the impedance Zt of the voltage control variable impedance element 32 is decreased. As a result, the pulse width of the pulse signal train S3 obtained from the waveform shaping circuit 4 is decreased, thereby checking the control voltage Vc from increasing. Conversely, when the pulse width of the pulse signal train S3 is decreased to decrease the control voltage Vc, the impedance Zt of the voltage control variable impedance element 32 is increased. As a result, the pulse width of the pulse signal train S3 obtained from the waveform shaping circuit 4 is increased, thereby checking the control voltage Vc from decreasing. That is, the first integrating circuit 51 degenerates the time constant controlled differentiating circuit 3, which in turn stabilizes the pulse signal train S3.

The integrating circuit 5 is also designed so that the second integrating circuit 52 integrates the pulse signal train S3 and outputs the voltage obtained by the integration as the humidity signal S4. Therefore, a linearized relative humidity-output voltage characteristic can be obtained.

Since the bias circuit 6 applies the bias voltage to the control electrode 323 of the voltage control variable impedance element 32, the bias circuit 6 ensures reliable operation of the voltage control variable impedance element 32 even if the control voltage Vc is low. Therefore, a shortage of the control voltage Vc can be supplemented by the bias voltage of the bias circuit 6, and the voltage control variable impedance element 32 can be operated to allow the impedance Zt to change exponentially. As a result, the differentiated signal S2 whose time constant changes exponentially can be obtained from both terminals of the main electrodes 321, 322 of the voltage control variable impedance element 32. Such differentiated signal S2 prevents variations in the voltage control variable impedance element in the low output range from adversely affecting the operation, thereby obtaining a relative humidity signal S4 having high linearity.

Figure 2:
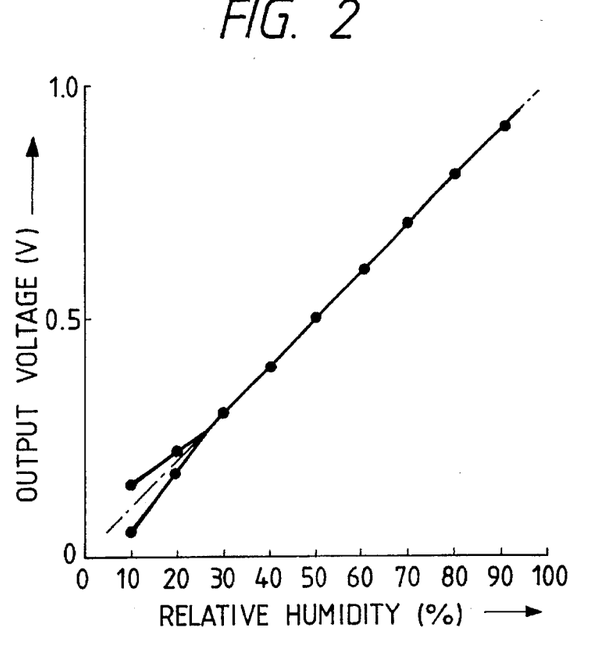
FIG. 2 is a diagram showing a characteristic of the humidity meter of the invention.
Figure 3:
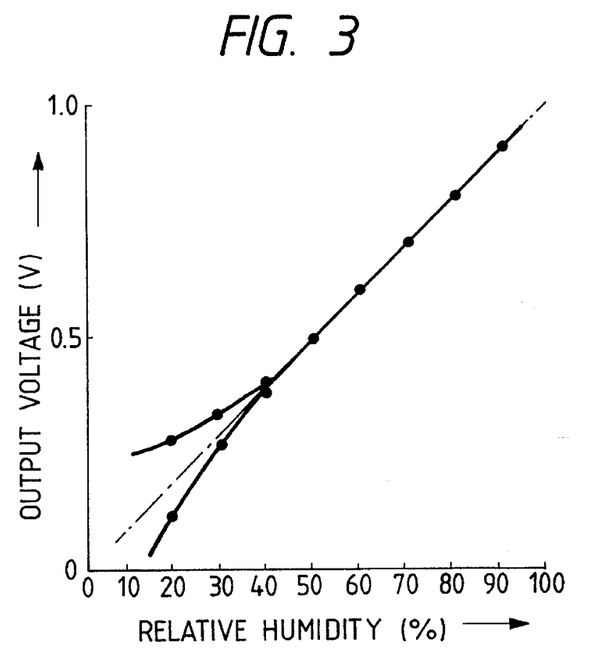
FIG. 3 is a diagram showing a characteristic of a conventional humidity meter.

FIG. 2 is a diagram showing a characteristic of the humidity meter of the invention and FIG. 3 is a diagram showing a characteristic of a conventional humidity meter. In FIGS. 2 and 3, the abscissa indicates the relative humidity and the ordinate indicates the output voltage of a humidity signal. A transistor is used as the voltage control variable impedance element 32. In the case of FIG. 2, the bias circuit is caused to have a base current of 0.1 to 1 μA. The solid circles represent a transistor whose current amplifying variations are minimum and indicates a case where the resistor 511 is appropriately adjusted. The solid squares represent a transistor whose current amplifying variations are maximum and indicates a case where the resistor 511 is appropriately adjusted. By comparing FIGS. 2 and 3, the humidity meter of the invention (FIG. 2) exhibits a remarkable improvement in the linearity in the relative humidity range of 50% or less owing to the positive effects brought about by the bias circuit 6, with the negative effects of variations being also limited.

Figure 4:
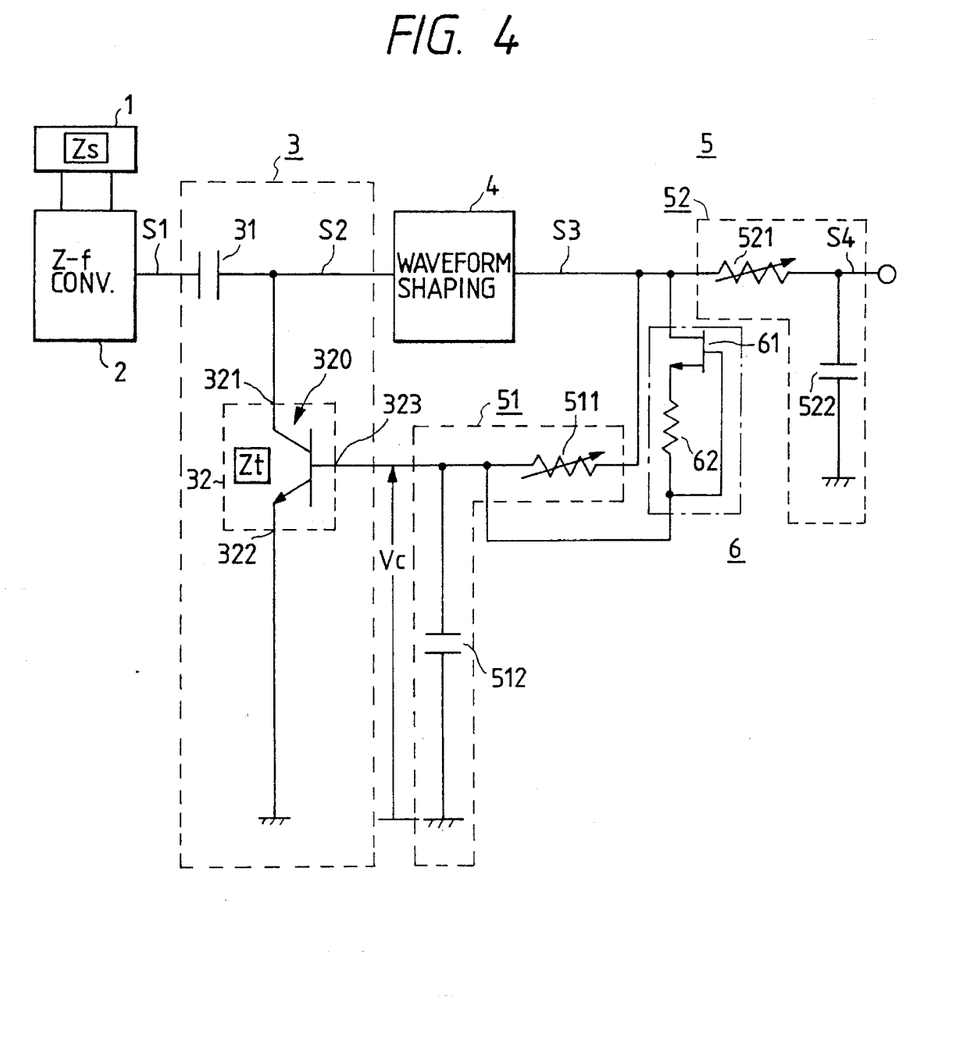
FIG. 4 is a block diagram of a humidity meter, which is another embodiment of the invention.

FIG. 4 is a block diagram of a humidity meter, which is another embodiment of the invention. In FIG. 4, the same reference numerals as those in FIG. 1 denote like parts and components.

In this embodiment, bias circuit 6 is operated by the pulse signal train S3 as a power supply thereof, and is implemented by a field-effect transistor 61 and a resistor 62. According to this configuration, the bias circuit 6 applies a bias voltage to the control terminal 323 only when the voltage control variable impedance element 32 is operated to differentiate the pulse signal S1. As a result, the bias voltage is applied only when the application of a bias voltage is necessary, which in turn contributes to improving the control characteristic of the voltage control variable impedance element 32. Since the peak value of the pulse signal train S3 is larger than the integrated control voltage Vc, the bias circuit 6 can apply the bias voltage reliably to the control terminal 323. In addition, power consumption of the bias circuit 6 can be reduced as well.

Figure 5:
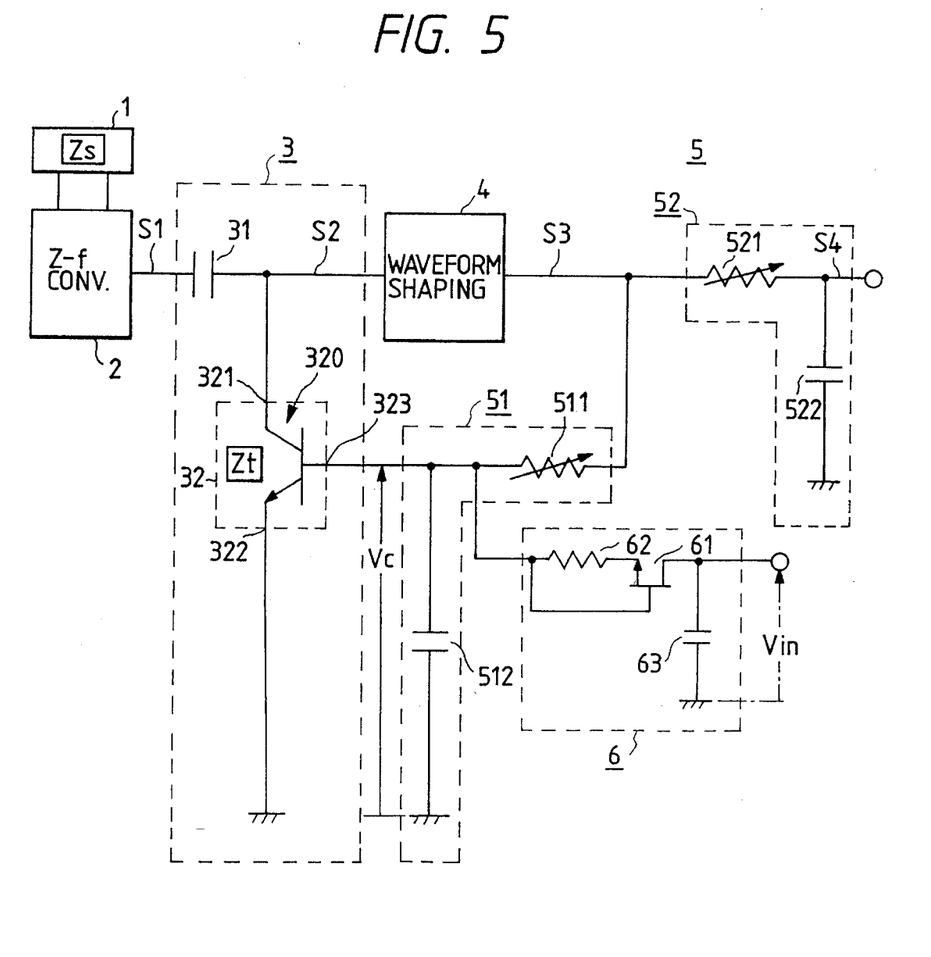
FIG. 5 is a block diagram of a humidity meter, which is still another embodiment of the invention.
Figure 6:
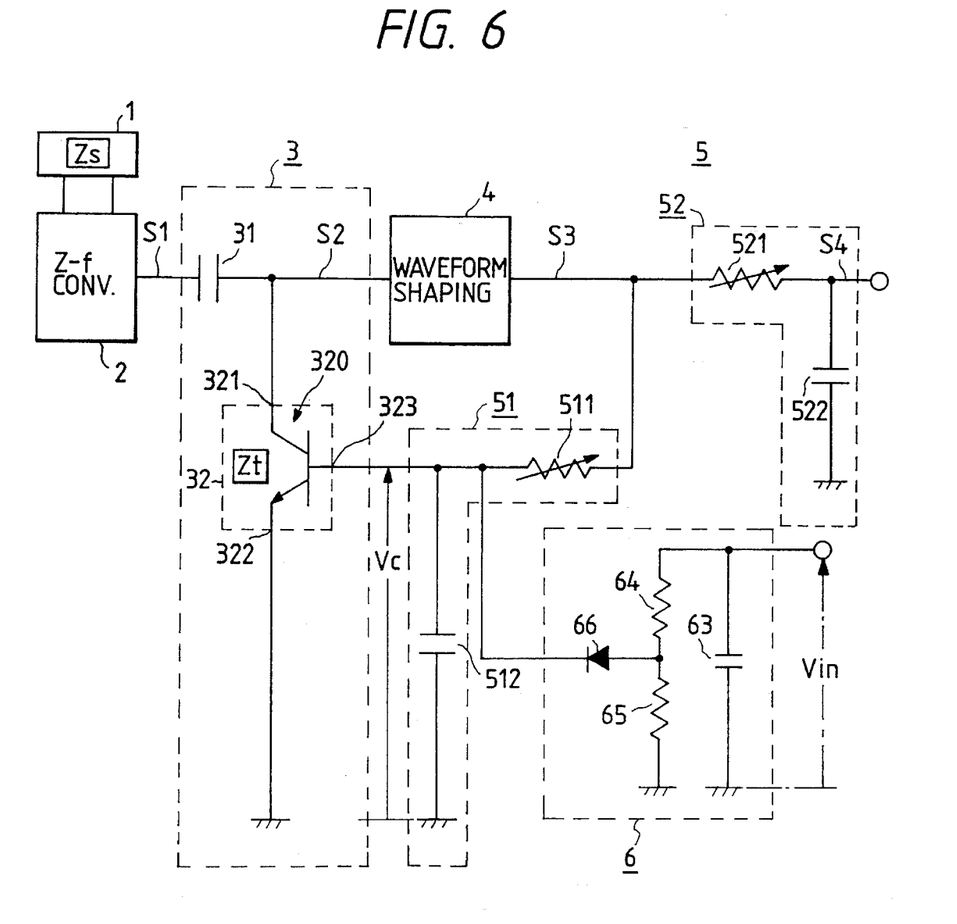
FIG. 6 is a block diagram of a humidity meter, which is still another embodiment of the invention.
Figure 7:
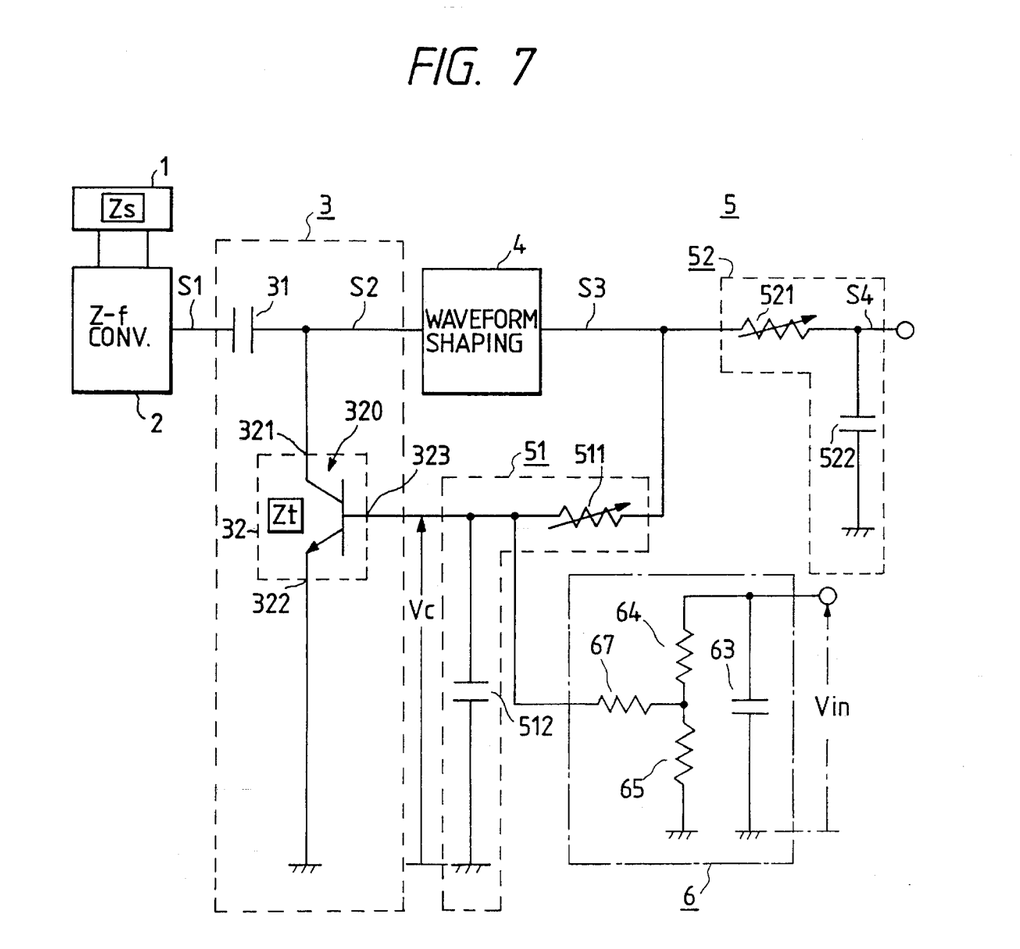
FIG. 7 is a block diagram of a humidity meter, which is still another embodiment of the invention.

FIGS. 5 to 7 are block diagrams of humidity meters, which are other embodiments of the invention. In FIGS. 5 to 7, the same reference numerals as those in FIGS. 1 and 4 denote like parts and components.

The embodiments shown in FIGS. 5 to 7 are designed to be operated by a dc power supply Vin. The bias circuit 6 of FIG. 5 includes a capacitor 63 to smooth the dc power supply Vin, and a field-effect transistor 61 and the resistor 62 to obtain a bias voltage from the dc power supply Vin. The bias circuit 6 of FIG. 6 includes a resistance dividing circuit consisting of a resistor 64 and a resistor 65 to divide the dc power supply Vin and supplying a current corresponding to the divided voltage of the resistor 65 to the control terminal 323. The divided voltage of the resistor 65 is set to a value smaller than the maximum control voltage Vc and larger than the minimum control voltage Vc. A diode 66 blocks reverse flow of current from a capacitor 512 to the resistor 65 to prevent the control voltage Vc from dropping. The bias circuit 6 of FIG. 7 replaces the diode 66 of FIG. 6 with a resistor 67 having high resistance.

Figure 8:
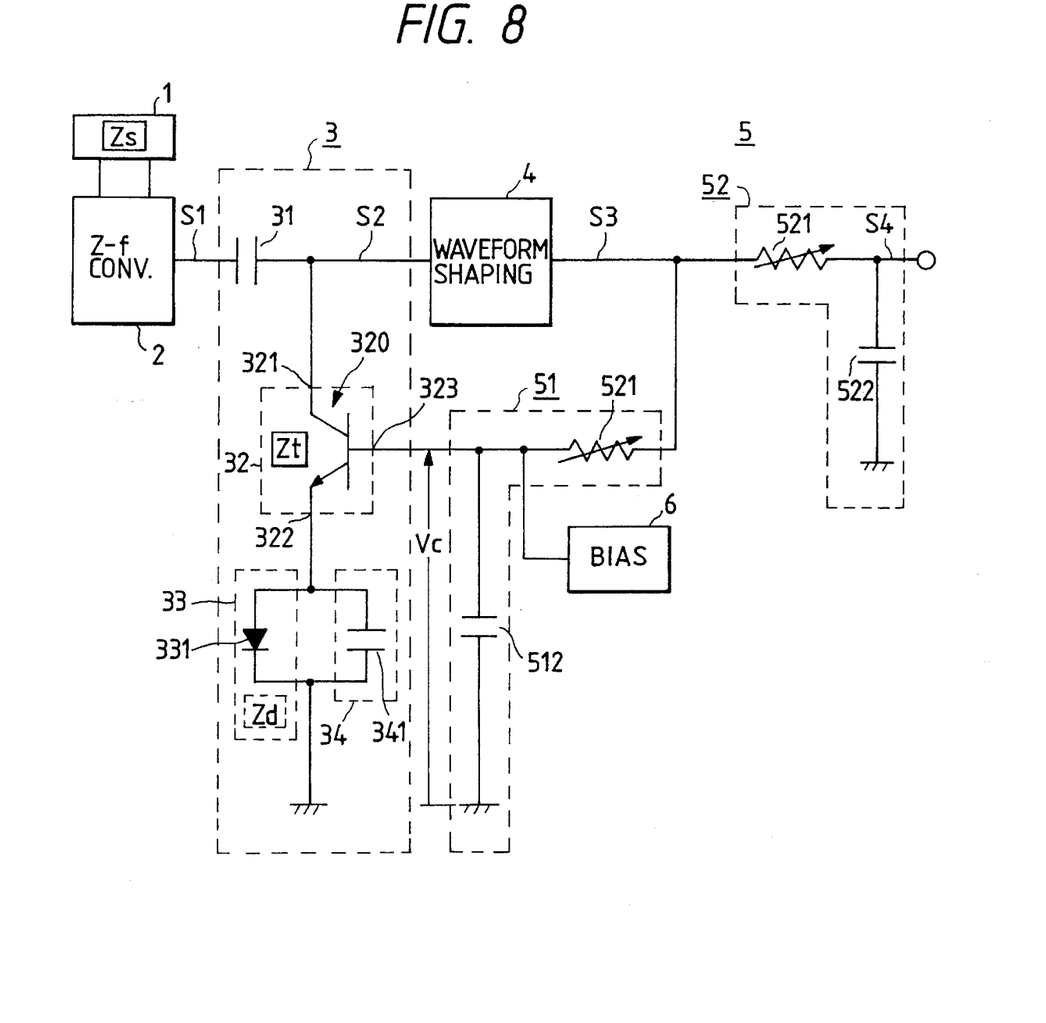
FIG. 8 is a block diagram of a humidity meter, which is still another embodiment of the invention.

FIG. 8 is a block diagram of a humidity meter of still another embodiment of the invention. In FIG. 8, the same reference numerals as those in FIG. 1 denote like parts and components.

The time constant controlled differentiating circuit 3 includes a nonlinear impedance element 33 whose impedance Zd is changed exponentially by an applied voltage. The nonlinear impedance element 33 has one terminal thereof connected to the main electrode 322, which is opposite to the main electrode 321 connected to the capacitor 31, and the other terminal thereof grounded. The time constant controlled differentiating circuit 3 outputs the differentiated signal S2 from both terminals of the voltage control variable impedance element 32 and the nonlinear impedance element 33 which are connected in series with each other.

In this embodiment, a shortage in the impedance Zt of the conventional voltage control variable impedance element 32 can be supplemented by the impedance Zd of the nonlinear impedance element 33 in correcting the nonlinearity of the humidity sensor 1, which in turn allows the differentiated signal S2 to be obtained. The differentiated signal follows changes in the impedances of the voltage control variable impedance element 32 and the nonlinear impedance element 33 and has a time constant which changes exponentially. Required at this instance is a control voltage Vc that is equal to a value obtained by adding a voltage drop of the nonlinear impedance element 33 to a voltage drop between the control electrode 323 and the main electrode 322 of the voltage control variable impedance element 32. It is the bias circuit 6 supplementing the control voltage Vc that ensures reliable operation of the voltage control variable impedance element 32 and the nonlinear impedance element 33. Therefore, the application of the control voltage Vc degenerates the voltage control variable impedance element 32 and the nonlinear impedance element 33, which in turn improves linearity of the relative humidity signal S4. The application of the bias voltage by the bias circuit 6 not only ensures reliable operation of the voltage control variable impedance element 32 and the nonlinear impedance element 33 in the low output range, but also prevents variations from adversely affecting the operation, which in turn allows a relative humidity signal S4 having high linearity to be obtained.

The nonlinear impedance element 33, supplementing the impedance of the voltage control variable impedance element 32 over the entire humidity range, can linearize not only the relative humidity-output voltage characteristic in the low output range but also the relative humidity-output voltage characteristic in the high output range.

Since the nonlinear impedance element 33 is connected in series with the voltage control variable impedance element 32, a large synthetic impedance is obtained. As a result, leak current due to temperature of the voltage control variable impedance element 32 can be controlled, and the effects of temperature upon the relative humidity-output voltage characteristic can be reduced.

In a preferred embodiment of the time constant controlled differentiating circuit 3, the voltage control variable impedance element 32 is implemented by a transistor 320, and the nonlinear impedance element 33 is implemented by a diode 331. The transistor 320 is such that the collector serves as the main electrode 321; the emitter serves as the main electrode 322; and the base serves as the control electrode 323. The anode of the diode 331 is connected to the emitter of the transistor 320, and the capacitor 31 is connected to the collector of the transistor 320. The control voltage Vc is supplied to the base of the transistor 320. A silicon diode, a Schottky barrier diode, or the like may be used as the diode 331.

Since the relationship between the base voltage and the emitter current of the transistor 320 is exponential in this embodiment, the impedance Zt of the transistor 320 in operation also changes exponentially according to the control voltage Vc supplied to the base. Since the relationship between the forward voltage and the forward current of the diode 331 is exponential, the impedance Zd of the diode 331 in operation also changes exponentially. As a result, the application of the control voltage Vc degenerates the transistor 320 and the diode 331, thereby improving linearity of the relative humidity signal S4. The application of the bias voltage by the bias circuit 6 not only ensures reliable operation of the transistor 320 and the diode 331 in the low output range, but also prevents variations from adversely affecting the operation, which in turn allows a relative humidity signal S4 having high linearity to be obtained.

The time constant controlled differentiating circuit 3 includes an impedance adjusting circuit 34. The impedance adjusting circuit 34 is connected in parallel with the nonlinear impedance element 33 and corrects the impedance Zd. In this embodiment, the impedance adjusting circuit 34 decreases the synthetic impedance when the corrected value of the impedance Zd is too large thus finely adjusting impedance Zd of the nonlinear impedance element 33.

In an embodiment in which the impedance adjusting circuit 34 is implemented by a capacitor, the impedance Zd of the nonlinear impedance element 33 can be finely adjusted in accordance with the frequency of the pulse signal S2.

In an embodiment in which the impedance adjusting circuit 34 is implemented by a resistor (not shown), the impedance Zd of the nonlinear impedance element 33 can be finely adjusted independently of the frequency of the pulse signal S2.

In an embodiment in which the impedance adjusting circuit 34 is implemented by a diode (not shown), the impedance Zd of the nonlinear impedance element 33 can be adjusted to a value that is equal to the reciprocal of an integer.

Figure 9:
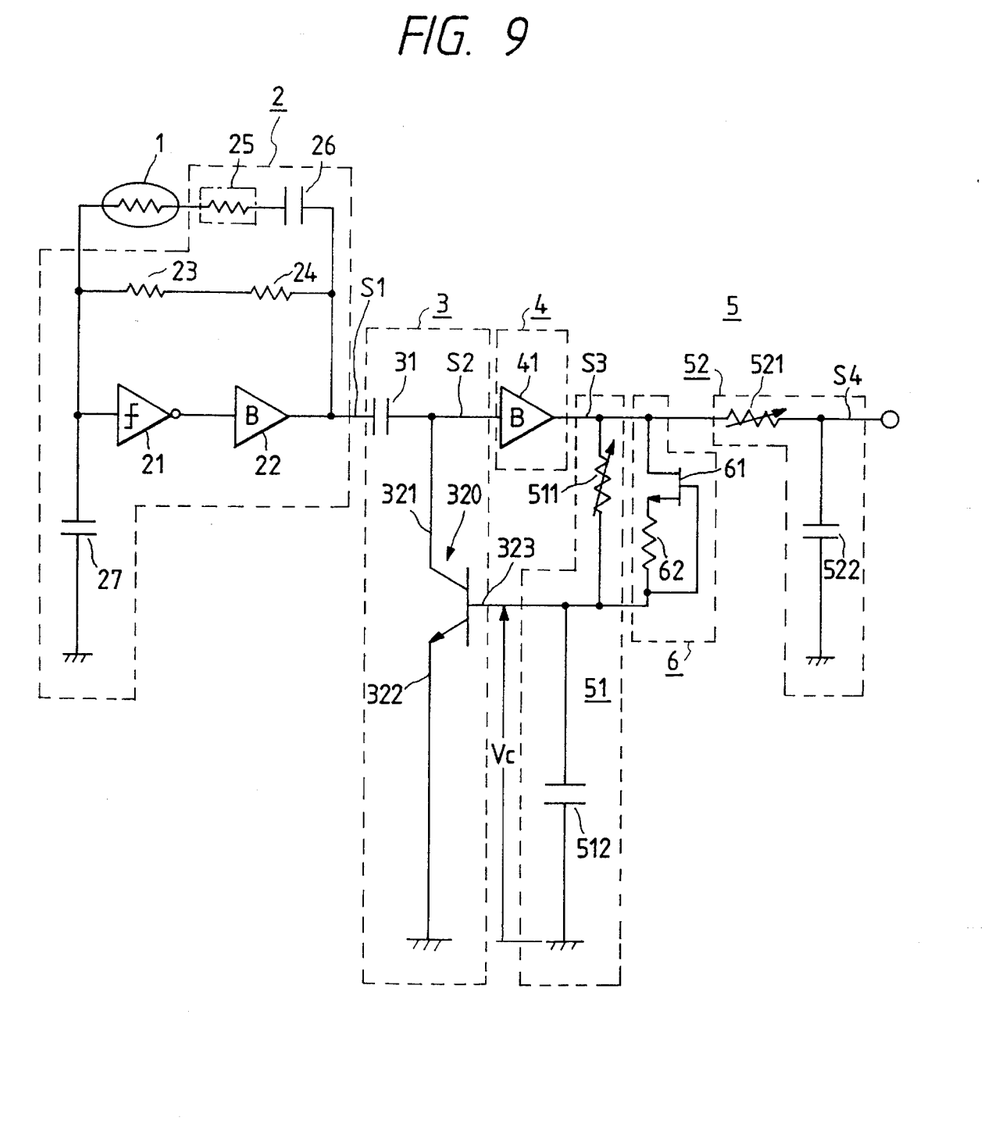
FIG. 9 is a specific circuit diagram of the humidity meter of the invention.

FIG. 9 is a specific circuit diagram of the humidity meter of the invention. This circuit diagram corresponds to the embodiment shown in FIG. 4. In FIG. 9, the same reference numerals as those in FIGS. 1 and 4 denote like parts and components.

The z–f conversion circuit 2 is comprised of a Schmitt trigger 21, a buffer 22, a resistor 23, a resistor 24, a thermistor 25, a capacitor 26, and a capacitor 27. The humidity sensor 1, the thermistor 25, and the capacitor 26 are connected in series with one another, one end of the humidity sensor 1 being connected to the input terminal of the Schmitt trigger 21 and one end of the capacitor 26 being connected to the output terminal of the buffer 22. The Schmitt trigger 21 and the buffer 22 are preferably implemented by ICs such as a CMOS and a TTL. The thermistor 25 compensates for changes due to temperature variations in the impedance Zs of the humidity sensor 1. The capacitor 26 blocks the flow of direct current. The buffer 22 decreases the output impedance of the Schmitt trigger 21, and shapes waveforms. The resistor 23 is connected in series with the resistor 24, with both ends of this series circuit connected to the input terminal of the Schmitt trigger 21 and the output terminal of the buffer 22, respectively. One end of the capacitor 27 is connected to the input terminal of the Schmitt trigger 21. As a result of this configuration, the z–f conversion circuit 2 is oscillated by the relationship between the impedances of the humidity sensor 1, the resistor 23, the resistor 24, the thermistor 25, and the capacitor 26 and the impedance of the capacitor 27, and outputs the pulse signal S1 whose frequency is in accordance with changes in the impedance of the humidity sensor 1.

The waveform shaping circuit 4 is implemented by a buffer 41. An IC such as a CMOS or a TTL is used as the buffer 41. The buffer 41 binary-codes the differentiated signal S2 with a threshold level as a predetermined voltage, and outputs the pulse signal train S3.

Figure 10:
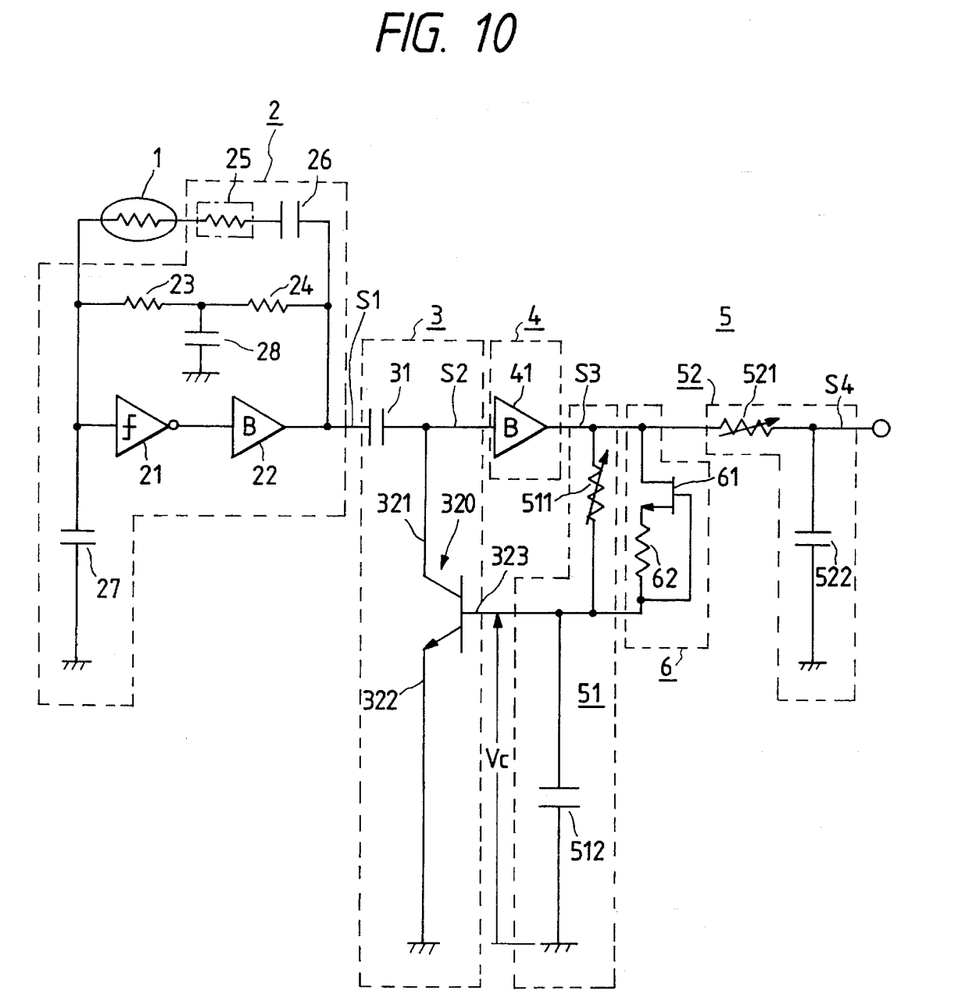
FIG. 10 is another specific circuit diagram of a humidity meter of the invention.

FIG. 10 is another specific circuit diagram of a humidity meter of the invention. In FIG. 10, the same reference numerals as those in FIG. 9 denote like parts and components. A capacitor 28 has one end thereof connected to a node between the resistor 23 and the resistor 24 which are connected in series with each other and the other end thereof grounded. According to this configuration, the ac component contained in a pulse signal is bypassed by the capacitor 28, so that the impedances at both ends of the series circuit formed of the resistor 23 and the resistor 24 can be maintained at high levels. This prevents the synthetic impedance of the series circuit, which is formed of the resistor 23 and the resistor 24, connected in parallel with the humidity sensor 1 from decreasing, which in turn allows the z–f conversion circuit 2 to convert a change in the impedance of the humidity sensor 1 into a pulse signal S1 efficiently.

Figure 11:
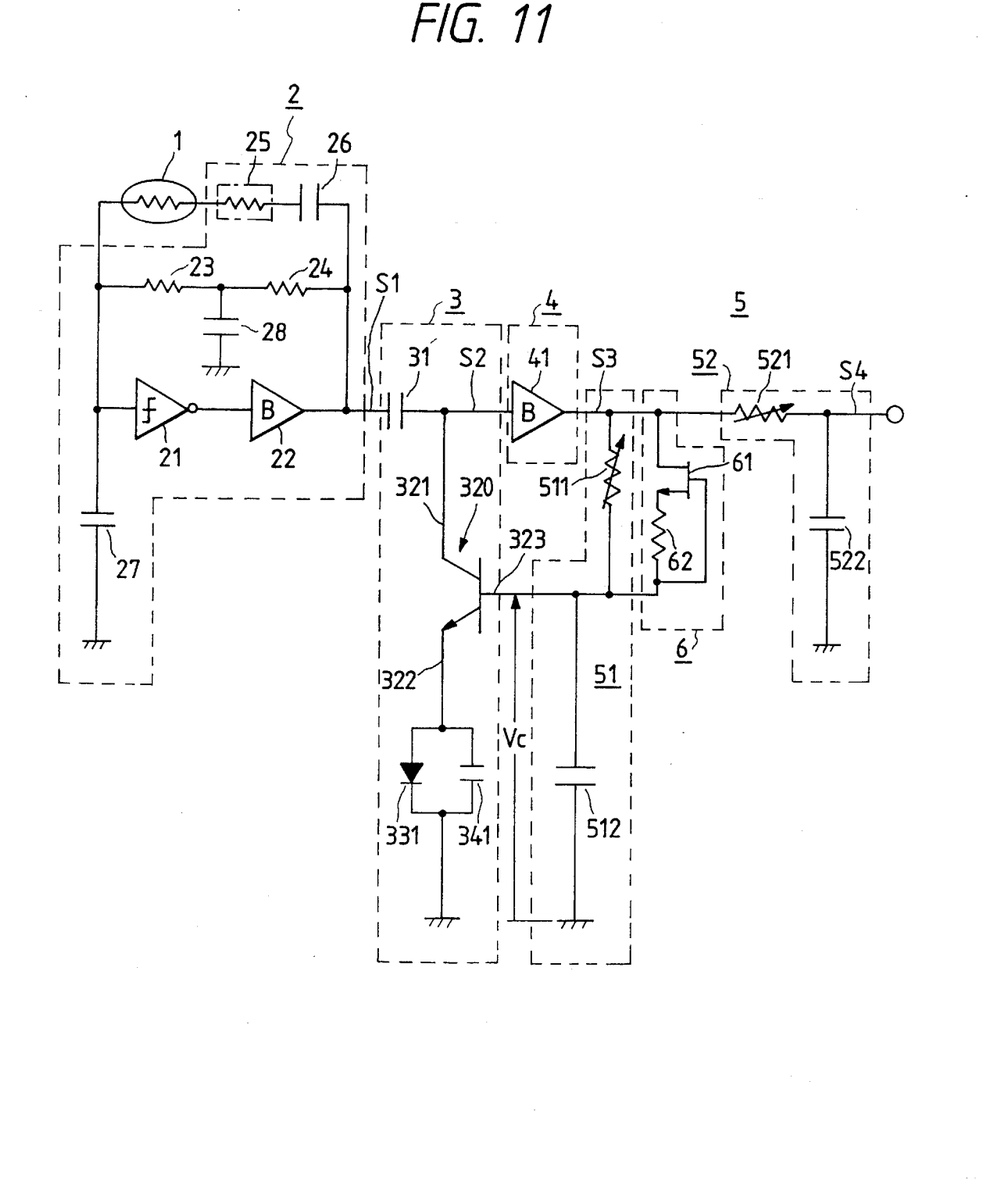
FIG. 11 is still another specific circuit diagram of the humidity meter of the invention.

FIG. 11 is still another specific circuit diagram of the humidity meter of the invention. The circuit diagram shown in FIG. 11 corresponds to the embodiment shown in FIG. 8. In FIG. 11, the same reference numerals as those in FIGS. 4, 8, and 10 denote like parts and components.

As described in the foregoing, the invention can provide the following advantages.

A humidity meter is capable of outputting a linearized humidity signal.

A humidity meter is capable of outputting a humidity signal having high linearity not only by ensuring reliable operation of the voltage control variable impedance element in the low output range, but also by preventing variations from adversely affecting the operation.

A humidity meter is capable of outputting a humidity signal having high linearity in the low output range by correcting inadequate linearity of the voltage control variable impedance element.

What is claimed is:

1. A humidity meter comprising:
   a humidity sensor having an impedance changing exponentially with respect to a relative humidity;

an impedance-frequency conversion circuit for generating a pulse signal whose frequency corresponds to the impedance of said humidity sensor;

a time constant controlled differentiating circuit including a capacitor having a terminal receiving the pulse signal and a voltage control variable impedance element being a three-terminal element having main electrodes and a control electrode with one of the main electrodes connected to an output of the capacitor, an impedance of said voltage control variable impedance element changing exponentially in accordance with a voltage applied to the control electrode, a differentiated signal obtained by differentiating the pulse signal being outputted from both of the main electrodes;

a waveform shaping circuit coupled with an output of said time constant controlled differentiating circuit, for generating a pulse signal train when the differentiation signal exceeds a predetermined threshold level;

an integrator including a first integrating circuit, coupled with an output of said waveform shaping circuit, for integrating the pulse signal train and supplying a voltage obtained by the integration to the control electrode of the voltage control variable impedance element, and a second integrating circuit, coupled with the output of said waveform shaping circuit, for integrating the pulse signal train and outputting a voltage obtained by the integration as a humidity signal; and a bias circuit for applying a bias voltage to the control electrode.

2. A humidity meter according to claim 1, wherein the bias circuit is operated by the pulse signal train as a power supply thereof.

3. A humidity meter according to claim 2, wherein said bias circuit comprises a field-effect transistor and a resistor which are disposed between the output of said a waveform shaping circuit and the control electrode of the voltage control variable impedance element.

4. A humidity meter according to claim 1, wherein said bias circuit comprises a smoothing capacitor, a field-effect transistor and a resistor, said bias circuit receiving a dc voltage from an external dc power source.

5. A humidity meter according to claim 1, wherein said bias circuit comprises a resistance dividing circuit including two resistors to divide a dc voltage from an external dc power source.

6. A humidity meter according to claim 5, wherein said bias circuit further comprises one of a diode and a resistor for blocking a reverse current from said first integrating circuit.

7. A humidity meter according to claim 1, wherein the time constant controlled differentiating circuit includes a nonlinear impedance element having two-terminals whose impedance is changed exponentially by an applied voltage, the nonlinear impedance element being connected to the main electrode opposite to the main electrode to which the capacitor is connected, and the differentiated signal being outputted from both terminals of the voltage control variable impedance element and the nonlinear impedance element connected in series with each other.

8. A humidity meter according to claim 7, wherein the time constant controlled differentiating circuit has an impedance adjusting circuit; and the impedance adjusting circuit is connected in parallel with the nonlinear impedance element.

9. A humidity meter according to claim 8, wherein the impedance adjusting circuit includes a capacitor.

10. A humidity meter according to claim 7, wherein the voltage control variable impedance element is implemented by a transistor, the nonlinear impedance element is implemented by a diode, an anode of the diode is connected to an emitter of the transistor, the capacitor is connected to a collector of the transistor; and the control voltage and the bias voltage are applied to a base of the transistor.

11. A humidity meter according to claim 10, wherein the impedance adjusting circuit includes a capacitor connected in parallel with the nonlinear impedance element.

* * * * *